United States Patent [19]

Esteve-Subirana

[11] 4,031,240
[45] June 21, 1977

[54] 2,5-DIHYDROXY BENZENE SULFONIC ACID MONO- AND DIESTERS

[75] Inventor: Antonio Esteve-Subirana, Barcelona, Spain

[73] Assignee: Laboratorios del Dr. Esteve S.A., Barcelona, Spain

[22] Filed: Sept. 12, 1975

[21] Appl. No.: 612,775

Related U.S. Application Data

[63] Continuation-in-part of Ser. No. 505,934, Sept. 13, 1974, Pat. No. 3,954,767, which is a continuation-in-part of Ser. No. 360,394, May 14, 1973, Pat. No. 3,876,651.

[30] Foreign Application Priority Data

May 17, 1975 Switzerland .................... 7327/75

[52] U.S. Cl. .................... 424/308; 260/247.1 R; 260/268 R; 260/294.8 F; 260/473 G; 424/248.5; 424/250; 424/263
[51] Int. Cl.² ........................ C07C 69/76
[58] Field of Search ............ 260/473 G, 247.1 R, 260/268, 294.8; 424/248, 250, 263, 308

[56] References Cited

UNITED STATES PATENTS

| | | | |
|---|---|---|---|
| 2,170,996 | 8/1939 | Grether et al. | 260/473 G |
| 3,448,110 | 6/1919 | Griot et al. | 260/473 G |
| 3,546,273 | 12/1970 | Bolhofer | 260/473 G |
| 3,625,950 | 12/1971 | Cragoe | 260/473 G |

*Primary Examiner*—Paul J. Killos
*Attorney, Agent, or Firm*—Henry L. Brinks

[57] ABSTRACT

Mono- and diesters of 2,5-dihydroxy benzene sulfonic acid are represented by the following formula:

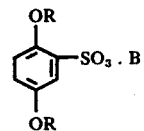

wherein each R residue is hydrogen or the residue of p-chlorophenoxy isobutyric acid having the formula:

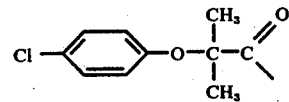

with the proviso that both Rs are not hydrogen simultaneously, and B is hydrogen or the equivalent of an inorganic or organic cation, these compounds are remarkable for their hypocholesterolemic, hypotriglycidemic and hypolipidemic activity.

18 Claims, No Drawings

2,5-DIHYDROXY BENZENE SULFONIC ACID MONO- AND DIESTERS

This application is a continuation-in-part of my copending application Ser. No. 505,934, filed Sept. 13, 1974, now U.S. Pat. No. 3,954,767 which in turn is a continuation-in-part of my application Ser. No. 360,394, filed May 14, 1973, now U.S. Pat. No. 3,876,651.

This invention concerns novel 2,5-dihydroxy benzene sulfonic acid mono- and diesters, and a process for preparing them.

These compounds have one of the following formula:

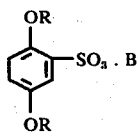

wherein each R residue is hydrogen or the residue of p-chlorophenoxy isobutyric acid having the formula:

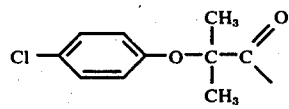

with the proviso that both Rs are not hydrogen simultaneously, and B is hydrogen or the equivalent of an inorganic or organic cation. B can be an alkali metal, an alkaline-earth metal, ammonia or unsubstituted or substituted amine cation, for instance alkanoylamines, alkyl- and aryl-amines, cyclic amines etc.

Compounds having this general formula possess extremely interesting pharmacodynamical properties. Particularly, they show a potent hypocholesterolemic, hypotriglycidemic, and hypolipidemic effect.

According to the invention, compounds having said general formula can be prepared by reacting a salt of p-dihydroxybenzene sulfonic acid with the chloride of p-chloro-phenoxy isobutyric acid.

The operation is effected preferably in an aprotic medium, generally a proton acceptor base such as pyridine, picoline, trimethylamine etc, to which may be added an organic solvent inert under the reaction conditions, for instance benzene, toluene, chloroform, diethyl ether, dimethylformamide, etc. Desirably the reaction is effected at a temperature between 20° and −10° C, preferably between 5° and −10° C. It is also possible to effect the reaction at a higher temperature, but then external cooling must be provided, since the reaction is exothermic.

While studying the reaction, one has observed that it can be performed starting from the sulfonic acid in free or salt form, although the yield of the operation is clearly higher when starting from the salt, than when starting from the free acid. It was also noted that the operation develops much better if, in addition to using a salt of the sulfonic acid, pyridine is used as the only solvent; in this way the pyridine salt of the desired compound is obtained with optimum yield. Starting from this pyridine salt, the other desired salts may be obtained by simple displacement.

All the thus obtained compounds can be separated from the reaction mixture in the usual manner, generally by simple filtration, optionally after preliminary decolorizing with charcoal, in the warm solution, and filtering while warm. They are then purified, e.g. by recrystallization.

The salts of magnesium, calcium and piperazine are preferred. They can be prepared simply by neutralizing sulfonic acid, for instance with magnesium or calcium carbonate, or with piperazine which can neutralize one or two molecules of the acid. The latter can be prepared from the pyridine salt, by treating said salt with concentrated sulfuric acid, preferably with approximately 18 N sulfuric acid, in the case of di-esters and mono-esters in the 5-position.

Mono-esterification in 2-position is effected starting from the calcium salt of 2,5-dihydroxy benzene sulfonic acid, thus the corresponding calcium salt is obtained directly. The magnesium or piperazine salts are prepared by neutralizing the mono-2-O-(p-chloro phenoxy isobutyroyl)-2,5-dihydroxy benzene sulfonic acid, obtained by treating the calcium salt with approximately 2N sulfuric acid.

The compounds according to this invention significantly inhibit the increase of plasma chlolesterol, triglycerides and total lipids contents in rats treated with Triton WR-1339 (Friedman N & Byers S. O., J. Exptl. Med., 97, 117, 1953; Garanttini S., Morpurgo C., Paoletti P. & Paoletti R., Arzneim.- forsch., 9, 206. 1959; Garattini S., Bizzi L., Grossi E. & Vertua R., "Drugs affecting Lipid Metabolism," Elsevier, 1961, p. 144-157). They significantly inhibit too the increase of plasma cholesterol and total lipids in white Leghorn chickens (Tennent D. M., Siegel H., Kuron G. W., Ott W. H. & Mushett C. W., Proc. Soc. Exptl. Biol. Med., 96, 679, 1957). The acute toxicities for the mouse are also very low. The medium lethal dose ($LD_{50}$) for the mouse was determined according to the modified method of Reed and Muench (Reed L. J. & Muench H., Am. J. Hyg., 27, 493, 1938).

The pharmacodynamical properties of the compounds described above are illustrated herebelow by those of the piperazine salt with one mole of the di-O-(p-chloro phenoxy isobutyrate) of 2,5-dihydroxy benzene sulfonic acid, prepared in Example 8 of this invention.

1. Acute toxicity in the mouse and rat
18 to 25 gr albino mouse.
100 to 150 gr. Sprague-Dawley rats.
The $LD_{50}$ was determined according to the method of Reed and Muench.

Table IV

| administration | species | $LD_{50}$ (mg/Kg) | fiducial limits (for p = 0,95) |
|---|---|---|---|
| oral | mouse ♂ | 11038 | (15502 – 7840) |
| oral | mouse ♀ | 8697 | (12931 – 5826) |
| oral | rat ♂ | 11000 | (12450 – 9713) |
| oral | rat ♀ | 11700 | (13120 – 10420) |

2. Hypolipemic action on the rat
The above-mentioned Triton WR-1339 method was selected. The total cholesterol, triglycerides and total lipids were determined in the scrum. The results obtained are given in Table V. The amount of Triton WR-1339 administered to the animals was 300 mg/Kg. The amount of the piperazine salt with one mole of the di-O-(p-chloro phenoxy isobutyrate) of 2,5-dihydroxy benzene sulfonic acid administered was 1 mMol/Kg orally. The letter P signifies probability.

Table V

| | Triton | Triton ↓ piperazine of di-O-(p-chloro phonoxy isobutyrate) of 2,5-dihydroxy benzene sulfonic acid |
|---|---|---|
| total cholesterol mg % ml of plasma | 283,3 | 212,5 |
| Δ% with respect to Triton | | −25 % |
| P | | 0,0025<P<0,005 |
| triglycerides mg % ml of plasma | 1122,5 | 572,5 |
| Δ% with respect to Triton | | −49 % |
| P | | 0,005<P<0,010 |
| total lipids mg % ml of plasma | 2088,6 | 1503,8 |
| Δ% with respect to Triton | | −28 % |
| P | | 0,005<P<0,010 |

EXAMPLE 1

In an erlenmeyer provided with stirring and refrigeration are placed 50–60 ml of 18 N sulfuric acid, and 13.8 g of the pyridine salt of the mono-O-(p-chloro phenoxy isobutyrate) of 2,5-dihydroxy benzene sulfonic acid are added, preferably the isomer esterified in 5-position, and this is left stirring at a low temperature for 10 minutes. Then 50 ml of ethyl ether are added, and stirring is continued until the two layers are completely clear. The two layers are separated by means of a dropping funnel, and the aqueous phase is extracted with 2 × 50 ml of ethyl ether. The organic phase is dried over anhydrous sodium sulfate, filtered, and evaporated at reduced pressure at 35° C. Thus 10.1 g of mono-O-(p-chlorophenoxy isobutyrate) of 2,5-dihydroxy benzene sulfonic acid are obtained in the form of an oil, whose infrared spectrum measured on a KBr tablet gives maxima at the following frequencies: 3290, 1740, 1480, 1220, 1110, 1000, 815 and 700 cm$^{-1}$.

EXAMPLE 2

To a solution of 1.0 g of piperazine hexahydrate in 10 ml of ethanol, a solution of 1.9 g of mono-O-(p-chloro phenoxy isobutyrate) of 2,5-dihydroxy benzene sulfonic acid, obtained according to Example 22, in 10 ml of ethanol, is added. The precipitate formed is filtered, and 2.1 g of the mono-salt of piperazine of mono-O-(p-chloro phenoxy isobutyrate) of 2,5-dihydroxy benzene sulfonic acid are obtained, in crystalline form having a melting point of 202°–205° C.

EXAMPLE 3

To a solution of 1.9 g of piperazine hexahydrate in 20 ml of ethanol, a solution of 7.5 g of mono-O-(p-chloro phenoxy isobutyrate) of 2,5-dihydroxy benzene sulfonic acid, obtained according to Example 22, in 20 ml of ethanol, is added. The precipitate formed is filtered, and 9.2 g of the di-salt of piperazine of mono-O-(p-chloro phenoxy isobutyrate) of 2,5-dihydroxy benzene sulfonic acid are obtained, in crystalline form, having a melting point of 245°–246° C.

EXAMPLE 4

To a solution of 3.8 g of mono-O-(p-chloro phenoxy isobutyrate) of 2,5-dihydroxy benzene sulfonic acid, obtained according to Example 22 in 15 ml of a 5:1 mixture (v/v) of ethanol and water, a slight excess of calcium carbonate is added. This is filtered and evaporated, and 3.8 g of the calcium salt of mono-O-(p-chloro phenoxy isobutyrate) of 2,5-dihydroxy benzene sulfonic acid are obtained in the form of a white powder whose infrared spectrum determined in a KBr tablet gives maxima at the following frequencies: 3480, 3180, 1770, 1750, 1490, 1220, 860 and 820 cm$^{-1}$.

EXAMPLE 5

To a solution of 3.8 g of mono-O-(p-chloro phenoxy butyrate) of 2,5-dihydroxy benzene sulfonic acid, obtained according to Example 22, in 15 ml of ethanol, a slight excess of basic magnesium carbonate is added. This is filtered, evaporated and 3.0 g of the magnesium salt of mono-O-(p-chloro phenoxy isobutyrate) of 2,5-dihydroxy benzene sulfonic acid are obtained in the form of a slightly hygroscopic white powder, having an infrared spectrum measured in a KBr tablet which has maxima at the following frequencies: 3390, 1750, 1480, 1230, 1170, 1020, 820 and 700 cm$^{-1}$.

EXAMPLE 6

To a solution of 263 g of diethylamine 2,5-dihydroxy benzene sulfonate in 500 ml of pyridine, 470 g of the chloride of p-chloro phenoxy isobutyric acid are added with stirring. The reaction is exothermic, but it is effected without refrigeration, letting it cool to ambiant temperature. A coloured precipitate forms, which is filtered and washed with water, and then copiously with ethanol. Thus 601 g of the pyridine salt of the di-O-(p-chloro phenoxy isobutyrate) of 2,5-dihydroxy benzene sulfonic acid are obtained in the form of a white crystalline powder having a melting point of 186°–188° C.

EXAMPLE 7

In an erlenmeyer provided with stirring and refrigeration, 50–60 ml of 18 N sulfuric acid are placed, 19.8 g of the pyridine salt of di-O-(p-chloro phenoxy isobutyrate) of 2,5-dihydroxy benzene sulfonic acid are added, and this is left stirring, at a low temperature, for 20 minutes. Then 50 ml of ethyl ether are added, and stirring is continued until the two layers are completely transparent. The two layers are separated in a dropping funnel, and the aqueous phase is extracted with 2 × 50 ml of ethyl ether. The organic phase is dried over anhydrous sodium sulfate, filtered, evaporated under reduced pressure, and 17.5 g of di-O-(p-chlorophenoxy isobutyrate) of 2,5-dihydroxy benzene sulfonic acid are obtained in the form of a viscous oil whose infrared spectra give maxima at the following frequencies: 3285, 2990, 1750, 1480, 1220, 1080, 1000, 820 and 705 cm$^{-1}$.

EXAMPLE 8

To a solution of 1.9 g of piperazine hexahydrate in 20 ml of ethanol, a solution of 6.0 g of di-O-(p-chlorophenoxyisobutyrate) of 2,5-dihydroxy benzene sulfonic acid obtained according to Example 28 in 10 ml of ethanol is added. The mixture is left in a refrigerator for 2 h, it is filtered, the product formed is recrystallized, and 4.3 g of the pierazine mono-salt of di-O-(p-chlorophenoxy isobutyrate) of 2,5-dihydroxy benzene sulfonic acid is obtained in the form of white crystals having a melting point of 168° C.

EXAMPLE 9

To a solution of 1.9 g of piperazine hexahydrate in 20 ml of ethanol, a solution of 12 g of di-O-(p-chlorophenoxy isobutyrate) of 2,5-dihydroxy benzene sulfonic acid obtained according to example 28 in 20 ml of ethanol is added. The precipitate formed is filtered, recrystallized and 9.8 g of the piperazine di-salt of di-O-(p-chlorophenoxy isobutyrate) of 2,5-dihydroxy benzene sulfonic acid is obtained in the form of white crystals having a melting point of 197°–200° C.

EXAMPLE 10

To a solution of 6.0 g of di-O-(p-chloro phenoxy isobutyrate) of 2,5-dihydroxy benzene sulfonic acid obtained according to Example 28 in 20 ml of ethanol, an excess of calcium carbonate is added, this is filtered, evaporated and 5.9 g of the calcium salt of di-O-(p-chlorophenoxy isobutyrate) of 2,5-dihydroxy benzene sulfonic acid is obtained in the form of white crystals whose infrared spectrum, measured on a KBr tablet, gives maxima at the following frequencies: 3520, 3400, 1750, 1480, 1230, 1080, 820 and 700 cm$^{-1}$.

EXAMPLE 11

To a solution of 6.0 g of di-O-(p-chloro phenoxy isobutyrate) of 2,5-dihydroxy benzene sulfonic acid obtained according to Example 28 in 20 ml of ethanol, a slight excess of basic magnesium carbonate is added, this is filtered, evaporated and 5.0 g of magnesium salt of di-O-(p-chloro phenoxy isobutyrate) of 2,5-dihydroxy benzene sulfonic acid is obtained in the form of a white powder whose infrared spectrum, measured in a KBr tablet, gives maxima at the following frequencies: 3400, 1760, 1650, 1480, 1230, 1090, 1020, 840, 820 and 705 cm$^{-1}$.

EXAMPLE 12

To a solution of 10.70 g (0.025 mole) of calcium 2,5-dihydroxy benzene sulfonate (containing 0.63 equivalents of $H_2O$) in 100 ml of acetone containing 4.5 ml of water, 20.55 g (0.050 mole) of p-chloro phenoxy isobutyric acid anhydride are added, and with stirring for 4 hours, 1.4 g (0.025 mole) of CaO are added portionswise (Ca content determined previously). A precipitate of calcium p-chloro phenoxy isobutyrate dihydrate forms gradually. After 5 hours reaction at room temperature, this is concentrated to dryness under reduced pressure, the amorphous residue is taken up in 200 ml of water at 2° C, it is left at this temperature for 2 hours, and then 12.0 g of calcium p-chloro phenoxy isobutyrate dihydrate is filtered off. The mother liquors are concentrated to dryness, under reduced pressure, and the amorpho-crystalline residue is crystallized with ether. The fraction thus obtained is soluble in tetrahydrofuran (THF), ethyl acetate acetone. It is recrystallized in the THF solution with ether.

The product crystallizes with one molecule of the solvent, e.g. THF, acetone, ethyl acetate. The crystallization solvent is removed at 100° C, 17 hours. Yield: 15.5 g (74%). The product, which exhibits polymorphism, is calcium 2-O-(p-chlorophenoxy isobutyryl) 2,5-dihydroxy benzene sulfonate. Coefficients of molecular extinction in UV:

$$\left. \begin{array}{l} \epsilon\ 223\ nm = 39,500 \\ \epsilon\ 280\ nm = \phantom{0}8,500 \end{array} \right\} s = H_2O$$

The infrared spectrum, measured with nujol, gives maxima at 3340, 1750, 1600, 1230, 1200, 1130, 1090, 1030, 870, 830 and 720 cm$^{-1}$.

EXAMPLE 13

To an aqueous solution of 93.48 g (0.11 mole) of calcium 2-O-(p-chloro phenoxy isobutyryl) 2,5-dihydroxy benzene sulfonate dihydrate, 110 ml of 2N sulfuric acid are added dropwise, with stirring; the suspension is cooled to 2° C for 120 minutes, $SO_4Ca$ is removed by filtering. To the clear filtrte 4.76 g (0.11 mole) of MgO are added with stirring. After a few minutes, the whole of the oxide was consumed. The solvent is removed under reduced pressure, and the amorphous residue is taken up in acetone. The remaining $SO_4Ca$ is filtered, the solvent is removed under reduced pressure, the evaporation residue is taken up in ether, wherefrom 91.0 g of magnesium 2-O-(p-chlorophenoxy isobutyryl) 2,5-dihydroxy benzene sulfonate crystallizes. This product is kept at 98° C for 17 hours. At room temperature, the ester re-equilibrates its $H_2O$ content. 83.8 g of magnesium 2-O-(p-chlorophenoxy isobutyryl) 2,5-dihydroxybenzene sulfonate dihydrate are obtained.

The infrared spectrum, measured with nujol, gives maxima at 3450, 1750, 1600, 1200, 1090, 1040, 1030, 970, 870, 840 and 720 cm$^{-1}$.

EXAMPLE 14

To a solution of 1.694 g (2 mmoles) of calcium 2-O-(p-chlorophenoxy isobutyryl) 2,5-dihydroxy benzene sulfonate in water, 2 ml of 2N sulfuric acid are added, the $SO_4Ca$ formed is removed by filtration, 172.2 mg (2 mmoles) of piperazine are added to the filtrate. This is evaporated to dryness under reduced pressure; the residue is taken up in acetone, a small amount of residual $SO_4Ca$ is removed by filtration, the filtrate is evaporated to dryness, and the piperazine salt is crystallized in ethyl acetate, and recrystallized in a mixture of tetrahydrofuran and ether. Bis-2-O-(p-chlorophenoxy isobutyryl)-2,5-dihydroxy benzene sulfonate of piperazine having a melting point of 226°–229° C is obtained.

EXAMPLE 15

To a solution of 0.8 g of diethylamine in 20 ml of ethanol, a solution of 6.0 g of di-O-(p-chloro phenoxy isobutyrate) of 2,5-dihydroxy benzene sulfonic acid in 10 ml of ethanol is added. The mixture is warmed, it is left to cool at ambient temperature, then in a refrigerator for 2 hours, it is filtered; the product formed is recrystallized and 4.3 g of the diethylamine salt of di-O-(p-chloro phenoxy isobutyrate) of 2,5-dihydroxy benzene sulfonic acid are obtained in the form of white crystals having a melting point of 176° C.

EXAMPLE 16

To a solution of 1.0 G of dipropylamine in 20 ml of ethanol, a solution of 6.0 g of di-O-(p-chloro phenoxy isobutyrate) of 2,5-dihydroxy benzene sulfonic acid in 10 ml of ethanol is added. The mixture is warmed, then left in a refrigerator for 4 hours, the product formed is recrystallized and 6.4 g of the dipropylamine salt of di-O-(p-chloro phenoxy isobutyrate) of 2,5-di-hydroxy benzene sulfonic acid are obtained in the form of white crystals having a melting point of 117° C.

EXAMPLE 17

To a solution of 1.3 g of dibutylamine in 20 ml of ethanol, a solution of 6.0 g of di-O-(p-chloro phenoxy isobutyrate) of 2,5-dihydroxy benzene sulfonic acid in 10 ml of ethanol is added. The mixture is warmed, then left in a refrigerator for 5 hours, it is filtered; the product formed is recrystallized and 4.2 g of the dibutylamine salt of di-O-(p-chloro phenoxy isobutyrate) of 2,5-dihydroxy benzene sulfonic acid are obtained in the form of white crystals having a melting point of 116° C.

EXAMPLE 18

To a solution of 0.8 g of morpholine in 20 ml of ethanol, a solution of 6.0 g of di-O-(p-chloro phenoxy isobutyrate) of 2,5-dihydroxy benzene sulfonic acid in 10 ml ethanol is added. The mixture is warmed, then left in a refrigerator for 5 hours, it is filtered; the product formed is recrystallized and 5.1 g of the morpholine salt of di-O-(p-chloro phenoxy isobutyrate) of 2,5-dihydroxy benzene sulfonic acid are obtained in the form of white crystals having a melting point of 160° C.

Because of the low toxicity of these compounds, and hence their high therapeutical index, their clinical performance is shown to be extremely interesting for the treatment of various types of hyperlipemia and dislipemia.

The pharmacodynamical properties of the compounds according to the invention are illustrated in the Table herebelow e.g. the medium lethal dose ($LD_{50}$), and the percent inhibition with respect to Triton WR-1339 of total cholesterol, triglycerides and total lipids. In this Triton WR-1339 method, all the compounds are administered at a dose of 2 mMoles/Kg orally excepted those compounds in which R is the residue of p-chloro-phenoxy isobutyric acid, which are administered orally at a dose corresponding to 2 mMoles of R per Kg, i.e. the amount used is calculated on the basis of the residue R only.

I claim:
1. Mono- and di-esters of salts of 2,5-dihydroxy benzene sulfonic acid, of general formula:

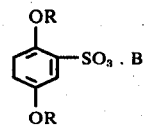

wherein each R residue is hydrogen or the residue of p-chloro phenoxy isobutyric acid of formula:

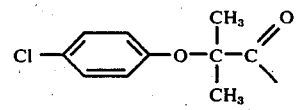

with the proviso that both Rs are not hydrogen simultaneously, and B is hydrogen or an equivalent of an inorganic or organic cation.

2. Mono-5-O-(p-chloro phenoxy isobutyroyl)-2,5-dihydroxy benzene sulfonic acid.

3. The calcium or magnesium salt according to claim 2.

4. The pyridine salt of the acid according to claim 2.

5. The piperazine salt of one or two moles of the acid according to claim 2.

6. Di-O-(p-chloro phenoxy isobutyroyl)-2,5-dihydroxy benzene sulfonic acid.

7. The pyridine salt of the acid according to claim 6.

8. The calcium or magnesium salt of the acid according to claim 6.

9. The piperazine salt of one or two moles of the acid according to claim 6.

10. The calcium salt of mono-2-O-(p-chloro phenoxy isobutyroyl)-2,5-dihydroxy benzene sulfonic acid.

11. The magnesium salt of mono-2-O-(p-chloro phenoxy isobutyroyl)-2,5-dihydroxy benzene sulfonic acid.

| | Percentage reduction of lipids | | | $LD_{50}$ |
|---|---|---|---|---|
| | Cholesterol | Triglycorides | Total Lipids | (mg/kg) |
| pyridine 2,5-dihydroxybenzenesulfonate mono-p-chloro phenoxy isobutyrate | 16 | 27 | 23 | 900 |
| mono-salt of piperazine of mono-O-(p-chloro phenoxy isobutyrate) of 2,5-dihydroxybenzenesulfonic acid | 9 | 49 | 25 | 4.300 |
| di-salt of piperazine of mono-O-(p-chloro phenoxy isobutyrate) of 2,5-dihydroxybenzenesulfonic acid | 16 | 31 | 26 | 4.700 |
| calcium salt of mono-O-(p-chloro phenoxy isobutyrate) of 2,5-dihydroxybenzenesulfonic acid | 27 | 40 | 26 | 4.500 |
| magnesium salt of mono-O-(p-chloro phenoxy isobutyrate) of 2,5 dihydroxybenzenesulfonic acid | 19 | 44 | 28 | 3.100 |
| pyridine salt of di-O-(p-chloro phenoxy isobutyrate) of 2,5-dihydroxybenzenesulfonic acid | 20 | 32 | 31 | 1.100 |
| piperazine mono-salt of di-O-(p-chloro phenoxy isobutyrate) of 2,5-dihydroxybenzenesulfonic acid | 25 | 49 | 28 | 11.000 |
| piperazine di-salt of di-O-(p-chloro phenoxy isobutyrate) of 2,5-dihydroxybenzenesulfonic acid | 29 | 21 | 37 | 8.000 |
| calcium salt of di-O-(p-chloro phenoxy isobutyrate) of 2,5-dihydroxybenzenesulfonic acid | 27 | 33 | 29 | 6.000 |
| magnesium salt of di-O-(p-chloro phenoxy isobutyrate) of 2,5-dihydroxybenzene sulfonic acid | 5 | 51 | 25 | 4.780 |
| calcium 2-O-(p-chloro phenoxy isobutyryl)-2,5-dihydroxybenzenesulfonate | 30 | 32 | 26 | 3.350 |
| magnesium 2-O-(p-chloro phenoxy isobutyryl)-2,5-dihydroxybenzenesulfonate | 18 | 21 | 27 | 2.450 |
| diethylamine salt of di-O-(p-chloro phenoxy isobutyrate) of 2,5-dihydroxy benzene sulfonic acid | 19 | 32 | 25 | 5,400 |
| dipropylamine salt of di-O-(p-chloro phenoxy isobutyrate) of 2,5-dihydroxy benzene sulfonic acid | 31 | 11 | 27 | 6,200 |
| dibutylamine salt of di-O-(p-chloro phenoxy isobutyrate) of 2,5-dihydroxy benzene sulfonic acid | 21 | 28 | 26 | 5,300 |
| morpholine salt of di-O-(p-chloro phenoxy isobutyrate) of 2,5-dihydroxy benzene sulfonic acid | 22 | 36 | 24 | 4,400 |

12. The piperazine salt with two moles of mono-2-O-(p-chloro phenoxy isobutyroyl)-2,5-dihydroxy benzene sulfonic acid.

13. The diethylamine salt of the acid according to claim 6.

14. The dipropylamine salt of the acid according to claim 6.

15. The dibutylamine salt of the acid according to claim 6.

16. The morpholine salt of the acid according to claim 6.

17. A medicament having a hypocholesterolemic, hypotriglycidemic, and hypolipidemic action, characterized in that it contains a compound as defined in claim 1, together with a pharmaceutically acceptable excipient.

18. A medicament according to claim 17, for oral administration, characterized in that it is in the form of a tablet or a capsule containing about 250 to 500 mg of active compound.

* * * * *

UNITED STATES PATENT AND TRADEMARK OFFICE
CERTIFICATE OF CORRECTION

PATENT NO. : 4,031,240
DATED : June 21, 1977
INVENTOR(S) : Antonio Esteve-Subirana It is certified that error appears in the above-identified patent and that said Letters Patent are hereby corrected as shown below:

Column 2, line 63, "scrum" should be -- serum --.

Column 4, line 26, "ambiant" should be -- ambient --.

Column 4, line 61, "pierazine" should be -- piperazine --.

Column 6, line 12, "filtrte" should be -- filtrate --.

Signed and Sealed this

Twentieth Day of June 1978

[SEAL]

Attest:

RUTH C. MASON
Attesting Officer

DONALD W. BANNER
Commissioner of Patents and Trademarks